United States Patent [19]

Cohen et al.

[11] Patent Number: 4,462,931

[45] Date of Patent: Jul. 31, 1984

[54] ENHANCED AQUEOUS CHEMILUMINESCENT SYSTEMS

[75] Inventors: Martin L. Cohen, White Plains, N.Y.; Frank J. Arthen, Jr., Washington; Shin-Shyong Tseng, Bridgewater, both of N.J.

[73] Assignee: American Cyanamid Company, Stamford, Conn.

[21] Appl. No.: 388,854

[22] Filed: Jun. 16, 1982

[51] Int. Cl.³ .............................................. C09K 11/06
[52] U.S. Cl. ................................. 252/700; 252/186.29
[58] Field of Search .............. 252/301.16, 700, 186.28, 252/186.29

[56] References Cited

U.S. PATENT DOCUMENTS

| | | | |
|---|---|---|---|
| 3,970,660 | 7/1976 | Bollyky | 252/301.16 |
| 3,973,466 | 8/1976 | Marcus et al. | 89/1 A |
| 3,974,086 | 8/1976 | Rauhut et al. | 252/301.16 |
| 4,053,430 | 10/1977 | Mohan | 252/188.3 |
| 4,282,357 | 8/1981 | Tseng et al. | 544/85 |
| 4,313,843 | 2/1982 | Bollyky | 252/188.3 |

Primary Examiner—Leland A. Sebastian
Assistant Examiner—Howard J. Locker
Attorney, Agent, or Firm—Gordon L. Hart

[57] ABSTRACT

Aqueous chemiluminescent systems are found to have improved chemiluminesence due to presence of surfactants in minor amounts.

6 Claims, No Drawings

ENHANCED AQUEOUS CHEMILUMINESCENT SYSTEMS

The invention described herein was made in the performance of work supported by the Office of Naval Research (Contract No. N-00014-77-C-0634), and is subject to the provisions of ASPR 7-104.18, December, 1969, and ASPR 7-302.23(b) long form, August, 1977.

This invention relates to novel processes and compositions for producing chemiluminescence, that is, the generation of electromagnetic radiation at wavelengths between 330 and 1000 nanometers by means of a chemical reaction. More particularly, it relates to novel processes and compositions for producing chemiluminescence in aqueous solutions and emulsions.

The generation of chemiluminescence by the reaction of an ester, or amide, of an oxalic acid with a source of hydrogen peroxide in the presence of a fluorescer compound in aqueous systems has been disclosed in U.S. Pat. Nos. 4,053,430 and 4,282,357. However, the emission intensities and the efficiencies of these systems are low. There is a need for aqueous chemiluminescent compositions having higher emission intensities, light capacities, and efficiencies.

In accordance with the present invention, there is provided a composition for generating chemiluminescent emission comprising an aqueous solution of (a) a water-soluble reactant, (b) a water-soluble organic fluorescer having a spectral emission in the range from about 330 to 1000 nanometers, and (c) a surfactant, in proportions capable of producing enhanced chemiluminescence on reaction with hydrogen peroxide.

The present invention also provides a composition for generating chemiluminescence comprising an oil-in-water emulsion of (a) a water-soluble reactant, (b) a water-insoluble organic fluorescer having a spectral emission in the range from about 330 to 1000 nanometers, and (c) a surfactant, in proportions capable of producing enhanced chemiluminescence on reaction with hydrogen peroxide.

The present invention further provides a composition for generating chemiluminescence comprising a dry mixture of (a) a water-soluble reactant, (b) a solid hydrogen peroxide source selected from the group consisting of sodium perborate, potassium perborate, sodium carbonate peroxyhydrate, and histidine perhydrate, (c) a solid water-soluble fluorescer having a spectral emission in the range from about 330 to 1000 nanometers, and (d) a surfactant, in proportions capable of producing enhanced chemiluminescence when added to water.

In all of the above compositions the reactant is preferably a water-soluble ester, or amide, of oxalic acid.

The present invention also provides processes for generating chemiluminescence by adding effective amounts of the aforedescribed compositions to an aqueous solution of hydrogen peroxide, or a source of hydrogen peroxide.

The processes of this invention produce quantum yields of about 1–8%, compared to about 0.7–1.5% for processes without the surfactant.

The aqueous chemiluminescent systems of the present invention provide enhanced emission of light which is useful in a wide variety of applications, particularly for providing emergency light at home, on highways, and at sea.

DESCRIPTION

The chemiluminescent reaction mixture contains a water-soluble reactant which generates light by reacting with hydrogen peroxide, or a source of hydrogen peroxide, in the presence of a fluorescer compound and a surface-active agent. Preferably, the reactant is a water-soluble ester, or amide, of oxalic acid.

Suitable water-soluble esters of oxalic acid which may be used in the present invention are disclosed by Mohan in U.S. Pat. No. 4,053,430.

Illustrative examples of suitable water-soluble esters of oxalic acid include the dihydrochlorides, dihydrobromides, dihydrofluorides, di(trifluoromethane) sulfonates, dimethanesulfonates, di-p-toluenesulfonates, dimethosulfates and diquaternary ammonium salts of the following compounds:

bis{2,6-dichloro-4-[(2-dimethylaminoethyl)methylsulfamoyl]phenyl}oxalate,
bis{2,4-dichloro-6-[(2-dimethylaminoethyl)methylsulfamoyl]phenyl}oxalate,
bis{2-chloro-4-[(2-dimethylaminoethyl)methylsulfamoyl]phenyl}oxalate,
bis{2-bromo-4-[(2-dimethylaminoethyl)methylsulfamoyl]phenyl}oxalate,
bis{2,6-dibromo-4-[(2-dimethylaminoethyl)methylsulfamoyl]phenyl}oxalate,
bis{3-fluoro-4-[(2-dimethylaminoethyl)methylsulfamoyl]phenyl}oxalate,
bis{2,4-dibromo-6-[(2-dimethylaminoethyl)methylsulfamoyl]phenyl}oxalate,
bis{2-fluoro-4-[(2-dimethylaminoethyl)methylsulfamoyl]phenyl}oxalate,
and the like.

The preferred water-soluble ester of oxalic acid is the dihydrochloride of bis{2,4-dichloro-6[(2-dimethylaminoethyl)methylsulfamoyl]phenyl}oxalate.

Suitable water-soluble amides of oxalic acid which may be used in the processes and compositions of this invention are disclosed by Tseng and Rauhut in U.S. Pat. No. 4,282,357.

Illustrative examples of suitable water-soluble amides of oxalic acid include the dihydrochlorides, dihydrobromides, dihydrofluorides, di(trifluoromethane) sulfonates, dimethanesulfonates, dimethosulfates, and ditetrafluoroborates of the following compounds:

N,N'-bis(2-morpholinoethyl)-N,N'-bis-(trifluoromethylsulfonyl)oxamide,
N,N'-bis(3-morpholinopropyl)-N,N'-bis(trifluoromethylsulfonyl)oxamide,
N,N'-bis[2-(2-pyridyl)ethyl]-N,N'-bis(trifluoromethylsulfonyl)oxamide,
N,N'-bis[3-(2-pyridyl)propyl]-N,N'-bis(trifluoromethylsulfonyl)oxamide,
N,N'-bis(6-morpholinohexyl)-N,N'-bis(trifluoromethylsulfonyl)oxamide,
N,N'-bis[2-(4-pyridyl)ethyl]-N,N'-bis(trifluoromethylsulfonyl)oxamide,
N,N'-bis[5-(3-pyridyl)pentyl]-N,N'-bis(trifluoromethylsulfonyl)oxamide,
and the like.

The preferred water-soluble oxamide is 4,4'-{oxalylbis[[(trifluoromethyl)sulfonyl]imino]ethylene}bis(4-methylmorpholinium trifluoromethanesulfonate).

The water-soluble fluorescer compounds, useful in the chemiluminescent compositions of this invention, may be defined broadly as compounds, having an emission spectral maximum between 330 and 1000 nanometers, which do not react with a hydrogen peroxide compound, or the amide, or ester, of oxalic acid, on contact. The water-soluble fluorescer may be anionic, cationic, or nonionic.

Illustrative examples of suitable fluorescers including the following:

Sulfonated 5,6,11,12-tetraphenylnaphthacene sodium salts,
4-methyl-4-[2-[1-oxo-4-(1-pyrenyl)butoxy]ethyl]morpholinium methyl sulfate,
4,4'-[9,10-anthracenediylbis(1,2-ethanediyl)]bisbenzenesulfonic acid disodium salt,
4,4'-[9,10-anthracenediylbis(1,2-ethanediyl)]bisbenzenemethanol bis(monosodium sulfate),
4,4'-[9,10-anthracenediylbis(1,2-ethynediyl)]bisbenzenecarboxylic acid dilithium salt,
4,4'-[6,12-diphenyl-5,11-tetracenediylbis(4,1-phenylenemethylene)]bis(4-methylmorpholinium methyl sulfate),
4,4'-[6,12-diphenyl-5,11-tetracenediylbis(4,1-phenylenemethylene)]bis(4-trifluoromethylmorpholinium trifluoromethyl sulfate),
2,8-bis[3,6,9-trioxadecyl)oxy]-5,11-bis[[3,6,9-trioxadecyl)oxy]phenyl]-6,12-diphenylnaphthacene,
and the like.

The preferred water-soluble fluorescer, referred to herein as sulfonated rubrene, is a mixture of sodium salts of sulfonated 5,6,11,12-tetraphenylnaphthacene.

Illustrative examples of suitable fluorescers which are not water-soluble include the following compounds:
5,6,11,12-tetraphenylnaphthacene,
9,10-bis(phenylethynyl)anthracene,
5,12-bis(phenylethynyl)tetracene,
9,10-diphenylanthracene,
perylene,
pyrene,
1-chloro-9,10-bis(phenylethynyl)anthracene,
2-chloro-9,10-bis(phenylethynyl)anthracene,
1,5-dichloro-9,10-bis(phenylethynyl)anthracene,
1,8-dichloro-9,10-bis(phenylethynyl)anthracene,
1-bromo-9,10-bis(phenylethynyl)anthracene,
1-fluoro-9,10-bis(phenylethynyl)anthracene,
2-methyl-9,10-bis(phenylethynyl)anthracene,
fluorescein,
rhodamine,
2,3-benzanthracene,
5,11-bis[4-(n-hexyl)phenyl]-6,12-diphenylnaphthacene,
5,11-bis[4-(n-dodecyl)phenyl]-6,12-diphenylnaphthacene,
5,11-bis[4-(2,5,8,11,14,17-hexaoctadec-1-yl)phenyl]-6,12-diphenylnaphthacene,
and the like.

The chemiluminescent reaction mixture contains about 0.1–5% by weight of an anionic, cationic, or non-ionic surface-active agent, herein also referred to as "surfactant," which is not rapidly oxidized by hydrogen peroxide. The terms "surface-active agent," or "surfactant," as used herein, are defined as substances that lower the surface tension of a liquid, or the interfacial tension between two liquids.

Illustrative examples of suitable surfactants include the following:
nonylphenoxy tetraethoxyethanol,
nonylphenoxy hexaethoxyethanol,
nonylphenoxy heptaethoxyethanol,
nonylphenoxy nonaethoxyethanol,
nonylphenoxy decaethoxyethanol,
octylphenoxy nonaethoxyethanol,
isooctylphenoxy decaethoxyethanol,
trimethylnonyl polyethyleneglycol ether,
sodium dodecylsulfate,
sodium diamylsulfosuccinate,
sodium dihexylsulfosuccinate,
sodium bis(2-ethylhexyl)sulfosuccinate,
sodium bis(tridecyl)sulfosuccinate,
disodium N-octadecylsulfosuccinamate,
sodium 2-ethylhexylsulfate,
sodium heptadecylsulfate,
n-dodecyltrimethylammonium chloride,
and the like.

Preferably, the reaction mixture contains about 0.75–3.5% by weight of a nonionic surfactant which is a nonylphenoxy polyethoxyethanol containing about 4 to 15 oxyethylene groups per molecule.

The initial molar concentrations (moles per liter of solution) of the oxalic acid ester, or amide, may vary considerably. It is only necessary that it be present in sufficient concentration to obtain chemiluminescence. The initial molar concentration is in the range of $10^{-3}$ to 5, preferably about $10^{-2}$ to 1.0.

The molar concentration of the fluorescer compound used is about $10^{-5}$ to 1, preferably about $10^{-3}$ to $10^{-1}$.

The initial molar concentration of the hydrogen peroxide compound used is from about $10^{-3}$ to 10.0, preferably about $10^{-1}$ to 4.0. The mole ratio of hydrogen peroxide to oxalic acid ester, or amide, used ranges from about 0.5 to 100, preferably about 20 to 60.

The ingredients of the chemiluminescent compositions of this invention are kept separated until chemiluminescence is desired, when they may be admixed in a single step or in a series of steps. The order of admixing of the ingredients is usually not critical. The hydrogen peroxide compound, surfactant, and fluorescer compound may be dissolved in water and the oxalic acid ester, or amide, added thereto as a solid, or in a suitable inert diluent, to initiate chemiluminescence. Alternatively, the oxalic acid ester, or amide, surfactant, and fluorescer compound may be dissolved in water, and the hydrogen peroxide compound added thereto to initiate chemiluminescence. Optionally, a solution of the hydrogen peroxide compound in water may be added to a solid mixture of oxalic acid ester, or amide, surfactant, and fluorescer compound to initiate chemiluminescence.

An illustrative example of a suitable mixture contains the following: 13.23% by weight of 4,4'-[oxalylbis[(trifluoromethylsulfonyl)imino]ethylene]bis[4-methylmorpholinium trifluoromethanesulfonate], 2.12% by weight of sulfonated rubrene, 2.65% by weight of Tergitol® Nonionic Surfactant NP-13, and 82.00% by weight of sodium perborate.

If the fluorescer compound is water-insoluble, such as rubrene, it may be dissolved in a suitable inert water-immiscible organic solvent, such as cyclohexane, and the solution added to an aqueous mixture of a hydrogen peroxide source, an effective amount of a surfactant, and a water-soluble reactant to produce a chemiluminescent emulsion.

The hydrogen peroxide source employed in the compositions and processes of this invention may be an aqueous solution of hydrogen peroxide per se, or a hydrogen peroxide-producing compound, such as sodium perborate, potassium perborate, sodium carbonate peroxyhydrate, histidine perhydrate, and the like.

Variation of the pH of the reaction medium from about 3.0 to about 8.4 shows that the quantum yield is dependent on the pH. The maximum quantum yield is obtained at a pH of 3.

Superior intensity of chemiluminescence is obtained when the final mixture producing the luminescence is maintained at a temperature from about −10° to 50° C., preferably from about 15° to 40° C.

The invention is described in more detail by the following examples in which concentrations in moles per liter are indicated by the letter "M." All parts, and percentages, are by weight unless otherwise indicated. In all of the examples which follow, the aqueous solution of hydrogen peroxide employed contains 1.75 moles per liter of hydrogen peroxide, and 0.0012 mole per liter of sodium salicylate, which catalyzes the reaction.

EXAMPLE 1

Preparation of Sulfonated Rubrene

A slurry of rubrene (10.0 grams; 0.0188 mole) in methylene chloride (250 mls) is stirred and cooled to 0°–5° C. in an ice-water bath. To the stirred slurry is added a solution of sulfur trioxide (4.1 grams; 0.0513 mole) in methylene chloride (50 mls) over a period of 90 minutes. The resulting reaction mixture is stirred at 0°–5° C. for one hour after the addition is completed and then added to a solution of sodium carbonate (11.7 grams; 0.11 mole) in water (250 mls).

The resulting mixture is stirred, and heated under an argon atmosphere to 80° C. to remove the methylene chloride, and then filtered through paper. The resulting filtrate is evaporated on a steam bath under a stream of argon and the resulting solid is dried and extracted with methanol (300 mls) in a Soxhlet extractor for 18 hours. The extraction solvent is then evaporated under vacuum to obtain 11.3 grams of solid product.

EXAMPLES 2–3

An aqueous solution of hydrogen peroxide (10 mls), containing 0.3540 gram of a nonionic polyether alcohol (DECERESOL® Surfactant NI Conc.; American Cyanamid Company), is prepared and a portion (2.6 mls) is added to a cuvette containing a mixture of 0.0165 gram of the product of Example 1, and 0.0929 gram of 4,4′-[oxalylbis[(trifluoromethylsulfonyl)imino]ethylene]bis[4-methylmorpholinium trifluoromethanesulfonate], hereafter referred to as METQ. The materials are mixed thoroughly at ambient temperature to provide a reaction mixture concentration of 0.01M for the product of Example 1, and an initial concentration of 0.0404M for the METQ. The emission intensity is then measured at the wavelength of maximum emission by means of a spectroradiometer-luminometer similar to that described by Roberts and Hirt [Appl. Spectrosc., 21, 250 (1967)] modified with a Jarrell-Ash Model 82-410 grating monochromator and an RCA C31034 photomultiplier with a gallium arsenide photocathode operated at 1300 V with dry ice cooling. Raw data are recorded digitally on a Hewlett-Packard 5150A thermal printer. Spectral response is corrected by calibration against a standard tungsten lamp. Absolute light intensities are obtained by deriving calibration constants based on the accepted fluorescence quantum yield (0.55) for quinine sulfate, as reported by Melhuish [N.Z. Sci. Tech., B, 37, 142 (1955)], in 0.1N $H_2SO_4$, and by ferrioxalate actinometry [Hatchard et al., Proc. R. Soc. London, Ser. A, 235, 518 (1956)] of the exciting light.

The light capacity (the light output in lumen hours per liter of emitting solution) is related to the chemiluminescence brightness and lifetime as described in U.S. Pat. No. 3,816,326.

Chemiluminescence percent quantum yields (einsteins per mole of reactant × 100) are calculated by monitoring the intensity decay at the emission maximum and calculating the intensity at each time interval in einsteins per second from the chemiluminescence spectrum. Chemiluminescence spectra are then corrected for intensity decay. The total area under the decay curve is calculated by using a combination of a Simpson's rule integration and an exponential extrapolation to infinite time as described by Roberts and Hirt. Data are processed by a Digital Equipment Corp. PDP-11/40 computer.

A comparison determination is also carried out, in the manner described above, without the surfactant. The results obtained are shown below under Examples 2 and 3, respectively.

| Example | 2 | 3 |
|---|---|---|
| Max (nm) | 585 | 580 |
| Light Capacity | 32 | 6.2 |
| Percent Quantum Yield | 3.79 | 0.75 |

Examination of the above results shows that the composition containing the surfactant is significantly superior in light capacity and quantum yield.

EXAMPLE 4

The procedure of Example 2 is followed in every detail except that 0.2253 gram of an anionic surfactant (AEROSOL® OT-75%; American Cyanamid Company) is substituted for the DECERESOL® NI Conc. The results obtained are shown below.

| Max (nm) | 570 |
|---|---|
| Light Capacity | 32 |
| Percent Quantum Yield | 3.52 |

EXAMPLE 5

The procedure of Example 2 is followed in every detail except that 0.1 gram of a cationic surfactant, n-dodecyltrimethylammonium chloride, is substituted for the DECERESOL NI Conc., and 0.0906 gram of METQ is used to provide an initial concentration of 0.0394M for the METQ. The results obtained are shown below.

| Max (nm) | 585 |
|---|---|
| Light Capacity | 9.4 |
| Percent Quantum Yield | 1.12 |

EXAMPLES 6–7

The procedure of Example 2 is followed except that 0.2615 gram of surfactant is utilized and the solution is added to a cuvette containing trisodium 8-hydroxy-1,3,6-pyrenetrisulfonate (0.0093 gram) and METQ (0.0906 gram) to provide a concentration of 0.0068M for the trisodium 8-hydroxy-1,3,6-pyrenetrisulfonate, and an initial concentration of 0.0394M for the METQ. A comparison determination is also carried out without the surfactant. The results obtained are shown below under Examples 6 and 7, respectively.

| Example | 6 | 7 |
|---|---|---|
| Max (nm) | 520 | 520 |
| Light Capacity | 0.24 | 0.12 |
| Percent Quantum Yield | 0.024 | 0.0097 |

The above results show that the composition containing the surfactant has a quantum yield and light capacity more than double that of a similar composition without the surfactant.

EXAMPLES 8-15

An aqueous solution of hydrogen peroxide (2.8 mls) is added to a cuvette containing 0.0178 gram of the product of Example 1, 0.10 gram of METQ, and 0.022 gram of the surfactant under test, to provide a concentration of 0.01M for the product of Example 1 and an initial concentration of 0.0404 for the METQ. The results obtained are shown in Table I.

TABLE I

| Example | Surfactant | Type | Max (nm) | Light Capacity | Percent Quantum Yield |
|---|---|---|---|---|---|
| 8 | DECERESOL ® NI Conc. | nonionic | 585 | 43 | 4.76 |
| 9 | Tergitol NP-4 | nonionic | 575 | 38 | 4.40 |
| 10 | Tergitol NP-6 | nonionic | 575 | 36 | 4.05 |
| 11 | Tergitol NP-10 | nonionic | 575 | 36 | 4.05 |
| 12 | Tergitol NP-7 | nonionic | 575 | 32 | 3.70 |
| 13 | Alipal EP 120 | anionic | 570 | 30 | 3.17 |
| 14 | Dowfax 2 AI | anionic | 585 | 27 | 2.99 |
| 15 | Sodium dodecylsulfate | anionic | 575 | 14 | 1.59 |

The above results illustrate the superior performance of the nonionic surfactants.

EXAMPLES 16-17

An aqueous solution of hydrogen peroxide (2.8 mls) is added to a cuvette containing 0.0178 gram of the product of Example 1, 0.022 gram of DECERESOL® Surfactant NI Conc., and 0.0982 gram of 2,2'[oxalylbis[[(trifluoromethylsulfonyl)imino]ethylene ]]bis[1-methyl-pyridinium trifluoromethanesulfonate], to provide a conentration of 0.01M for the product of Example 1, and an initial concentration of 0.0394M for the reactant. A comparison determination is also carried out without the surfactant. The results obtained are shown below.

| Example | 16 | 17 |
|---|---|---|
| Max (nm) | 575 | 575 |
| Light Capacity | 63 | 11 |
| Percent Quantum Yield | 6.96 | 1.41 |

EXAMPLE 18

An aqueous solution of hydrogen peroxide (2.3 mls) is added to a cuvette containing 0.0178 gram of the product of Example 1, 0.1 gram of METQ, 0.5 ml of cyclohexane, and 0.0221 gram of DECERESOL ® Surfactant NI Conc. The materials are mixed thoroughly at ambient temperature to provide an emulsion having an initial concentration of 0.0404M for the METQ, and a concentration of 0.01M for the product of Example 1. The results obtained are shown below.

| Max (nm) | 585 |
|---|---|
| Light Capacity | 39 |
| Percent Quantum Yield | 4.32 |

EXAMPLE 19

The procedure of Example 18 is followed in every detail except that the product of Example 1 is replaced by 0.0149 gram of rubrene. The results obtained are shown below.

| Max (nm) | 590 |
|---|---|
| Light Capacity | 59 |
| Percent Quantum Yield | 6.25 |

EXAMPLE 20

Preparation of 4-Methyl-4-[2-[1-oxo-4-(1-pyrenyl)butoxy]ethyl]morpholinium Methyl Sulfate

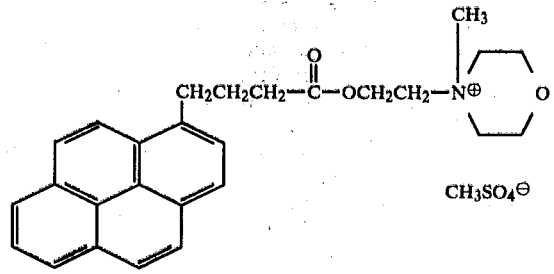

Dimethyl sulfate (6 mls; 0.063M) is added dropwise to a solution of 4-[2-[1-oxo-4-(1-pyrenyl)butoxy]ethyl]morpholine (2.64 grams; 0.006M) in dry acetone (50 mls) at 0° C., and the resulting reaction mixture is then heated at 50° C. for 1.5 hours. The reaction mixture is cooled to ambient temperature and filtered to recover a precipitate of the desired compound which weighs 2.28 grams, after drying in a vacuum oven, and melts at 115°-117° C.

Calculated for $C_{28}H_{33}NO_7S$: C,63.74%; H,6.30%; N,2.65%; Found: C,63.27%; H,6.26%; N,2.38%.

EXAMPLES 21-22

The procedure of Example 8 is followed in every detail except that 0.0148 gram of 4-methyl-4[2-[1-oxo-4-(1-pyrenyl)butoxy]ethyl]morpholinium methyl sulfate is substituted for the product of Example 1. A comparison determination is also carried out without the surfactant. The results obtained are shown below.

| Example | 21 | 22 |
|---|---|---|
| Max (nm) | 500 | 505 |
| Light Capacity | 5.6 | 0.37 |
| Percent Quantum Yield | 0.77 | 0.04 |

EXAMPLES 23-24

An aqueous solution of hydrogen peroxide (2.8 mls) is added to a cuvette containing 0.0178 gram of the product of Example 1, 0.0859 gram of bis{2,4-dichloro-6-[(2-dimethylaminoethyl)methylsulfamoyl]phenyl}oxalate dihydrochloride, and 0.0221 gram of DECERESOL ®

Surfactant NI Conc. The materials are mixed thoroughly at ambient temperature to provide an initial concentration of 0.04M for the bis{2,6-dichloro-6-[(2-dimethylaminoethyl)methylsulfamoyl]phenyl}oxalate dihydrochloride, and a concentration of 0.01M for the product of Example 1. A comparison determination is also carried out without the surfactant. The results obtained are shown below.

| Example | 23 | 24 |
| --- | --- | --- |
| Max (nm) | 595 | 605 |
| Light Capacity | 33 | 4.4 |
| Percent Quantum Yield | 4.40 | 0.62 |

EXAMPLE 25

Qualitative evaluation of the effect of surfactant on chemiluminescence is carried out by mixing 2.6 mils of an aqueous solution of hydrogen peroxide, 0.0165 gram of the product of Example 1, and 0.1963 gram of the bis(tetramethylammonium) salt of bis(2,3,6-trichloro-4-sulfophenyl)oxalate to initiate chemiluminescence. Addition of 0.1031 gram of DECERESOL NI Conc. to the mixture significantly enhances the intensity of light emission.

EXAMPLE 26

A solid mixture is prepared by blending 0.04 gram of the product of Example 1, 0.25 gram of METQ, 0.05 gram of DECERESOL® Surfactant NI Conc., and 1.55 grams of sodium perborate at room temperature in a 50 ml beaker. The addition of water (10 mls) to the beaker immediately produces a strong emission of a yellow-orange colored light.

EXAMPLE 27

The procedure of Example 26 is followed in every detail except that 0.05 gram of Tergitol® Nonionic Surfactant NP-13 (Union Carbide Corporation) is substituted for the DECERESOL® Surfactant NI Conc. Similar results are obtained.

We claim:

1. A composition for generating chemiluminescence comprising, in aqueous solution:
   (a) $10^{-3}$ to 5 molar concentration of a water-soluble reactant which generates light by reaction with hydrogen peroxide,
   (b) $10^{-5}$ to one molar concentration of a water-soluble or water dispersible organic fluorescer having spectral emission in the range about 300 to 1000 nanometers and,
   (c) 0.1 to 5% by wt of a surfactant, capable of producing enhanced chemiluminescence on reaction with hydrogen peroxide.

2. A dry mixture of components for making a chemiluminescent reaction by addition of the dry mixture to water, said dry mixture comprising:
   (a) a water-soluble reactant which generates light by reaction with hydrogen peroxide,
   (b) a water-soluble or water dispersible organic fluorescer having spectral emission in the range from 300 to 1000 nanometers and,
   (c) a surfactant, in proportions for making solution comprising the composition defined by claim 1 and
   (d) a solid hydrogen peroxide source selected from the group consisting of sodium perborate, potassium perborate, sodium carbonate peroxyhydrate, and histidene perhydrate.

3. A composition defined by claim 1 wherein the defined fluorescer is sulfonated rubrene.

4. A composition defined by claim 1 wherein the surfactant is a nonionic surfactant.

5. A method for producing chemiluminescence comprising dispersing a dry mixture defined by claim 2 in water.

6. A method for producing chemiluminescence comprising combining a composition defined by claim 1 with hydrogen peroxide or a source for hydrogen peroxide in aqueous solution.

* * * * *